(12) United States Patent
Burchardt et al.

(10) Patent No.: US 6,750,202 B1
(45) Date of Patent: Jun. 15, 2004

(54) PHOSPHINATE PEPTIDE ANALOGS FOR THE TREATMENT OF FIBROTIC DISORDERS

(75) Inventors: Elmar-Reinhold Burchardt, Schwerte (DE); Michael Schauer, Hilden (DE); Walter Stöcker, Nottuln (DE); Thomas Lampe, Wuppertal (DE)

(73) Assignee: Elmar R. Burchardt, Wuppertal (DE)

( * ) Notice: Subject to any disclaimer, the term of this patent is extended or adjusted under 35 U.S.C. 154(b) by 0 days.

(21) Appl. No.: 09/830,741
(22) PCT Filed: Oct. 28, 1999
(86) PCT No.: PCT/EP99/08181
§ 371 (c)(1), (2), (4) Date: Jun. 21, 2001
(87) PCT Pub. No.: WO00/27377
PCT Pub. Date: May 18, 2000

(30) Foreign Application Priority Data

Oct. 30, 1998 (DE) ......................... 198 50 072

(51) Int. Cl.$^7$ ............. C07K 5/06; C12N 9/64; A61K 38/05; A61K 1/16
(52) U.S. Cl. .............. 514/17; 530/232; 530/330; 530/332; 548/413
(58) Field of Search .............. 514/17, 18, 19; 530/323, 330, 331, 332; 548/413

(56) References Cited

FOREIGN PATENT DOCUMENTS

| EP | 0854191 | 7/1998 | ........... C12N/15/57 |
| WO | 9808853 | 3/1998 | ........... C07F/9/36 |

OTHER PUBLICATIONS

Yiallouros, I.; Vassiliou, S.; Yiotakis, A.; Zwilling, R.; Stocker, W.; and Dive Vincent, "Phosphinic Peptide the First Potent Inhibitors of Astacin Behave as Extremely Slow–Binding Inhibitors", Biochen. J., 331: 375–379 (Arp. 1998).

Bond, J. S., and Beynon, R. J., "The Astacin Family of Metalloendopeptidases", Prot. Sci., 4(7): 1247–1261 (1995).

Yiotakis, A.; Vassiliou, S.; Jiracek, J.; and Dive, V., "Protection of the Hydroxyphophinyl Function ofPhosphinic Dipeptides by Adamantyl. Application to the Solid–Phase Synthesis of Phosphinic Peptides", J. Org. Chem., 61(19): 6601–6605 (1996).

Kessler, E., Takahara, K., Biniaminov, L., Brusel, M., Greenspan, D. S., "Bone Morphogenetic Protein–1: The Type 1 Procollagen C–Proteinase", Science, 271: 360–362 (Jan. 1996).

Panchenko, M. V., Stetler–Stevenson, W. G., Trubetskoy, O. V., Gacheru, S. N., Kagan, H. M., "Metalloproteinse Activity Secreted by Fibrogenic Cells in the Processing of Prolysyl Oxidase", J. Biol. Chem., 271(12): 7113–7119 (1996).

Suzuki, N., Labosky, P. A., Furuta, Y., Hargett, L., Dunn, R., Fogo, A. B., Takahara, K., Peters, D. M., Greenspan, D. S., Hogan, B. L. M., "Failure of ventral body wall closure in mouse embryos lacking a procollagen C–proteinase encoded by Bmpl. mammalian gene related to Drosophila tolloid", Development, 122: 3587–2595 (1996).

Olsen, B. R., "Morphogenesis: Collagen it takes and bone it makes", Current Biology, 6(6): 645–647 (1996).

(List continued on next page.)

Primary Examiner—Jeffrey E. Russel (57) ABSTRACT

The invention relates to a method of treating a fibrotic disease, comprising administering to a mammal an effective amount of a phospinate-peptide analog of the general formula (I).

4 Claims, 3 Drawing Sheets

OTHER PUBLICATIONS

Gerling, B., Becker, M., Waldschmidt, J., Rehmann, M., Schuppan, D., "Elevated serum aminoterminal procollagen type–III–peptide parallels collagen accumulation in rats with secondary biliary fibrosis", Journal of Hepatology, 25: 79–84 (1996).

Kountouras, J., Billing, B. H., Scheuer, P. J., "Prolonged bile duct obstruction: a new experimental model for cirrhosis in the rat", Br. J. Exp. Path., 65: 305–311 (1984).

McLean, E. K., McLean, A. E. M., Sutton, P. M., "Instant Cirrhosis. An Improved Method for Producing Cirrhosis of the Liver in Rats by Simultaneous Administration of Carbon Tetrachloride and Phenobarbitone", Br. J. Exp. Path., 50: 502–506 (1969).

Johnson, S. J., Hines, J. E., Burt, A. D., "Phenotypic modulation of perisinusoidal cells following acute liver injury: a quantitative analysis", Int. J. Exp. Path., 73: 765–772 (1992).

Bickett, D. M., Green, M. D., Berman, J., Dezube, M., Howe, A. S., Brown, P. J., Roth, J. T., and McGeehan, G. M., A High Throughput Fluorogenic Substrate for Interstitial Collagenase (MMP–1) and Gelatinase (MMP–9), Analytical Biochemistry, 212: 58–64 (1993).

Grant, G. A., Eisen, A. Z., Marmer, B. L., Roswit, W. T., and Goldberg, G. I., "The Activation of Human Skin Fibroblast Procollagenase", The Journal of Biological Chemistry, 262(12): 5886–5889 (1987).

Aimes, R. T., Quigley, J. P., "Matrix Metalloproteinase–2 is an Interstitial Collagenase", J.Biol.Chem., 270(11): 5872–5876 (1995).

Prockop, D. J., Sieron, A. L, Li, S.–W., "Procollagen N–Proteinase and Procollagen C–Proteinase. Two Unusual Metalloproteinases that are Essential for Procollagen Processing Probably have Important Roles in Development and Cell Signaling", Matrix Biology, 16: 399–408 (1997/98).

Wozney, J. M., Rosen, V., Celeste, A. J., Mitsock, L. M., Whitters, M. J., Kriz, R. W., Hewick, R. M., Wang, E. A., "Novel Regulators of Bone Formation: MolecularClones and Activities", Science, 242: 1528–1534 (Dec. 1988).

Matayoshi, E. D., Wang, G. T., Krafft, G. A., Erickson, J., "Novel Fluorogenic for Assaying Retroviral Proteases by Resonance Energy Transfer", Science, 247: 954–958 (Feb. 1990).

Lee, S.–T., Kessler, E., and Greenspan D. S., "Analysis of Site–directed Mutations in Human Pro–α2(1) Collagen which Block Cleavage by the C–proteinase", J. Biol. Chem., 265(35): 21992–21996 (1990).

Campagne, J.–M., Coste, J., Guillou, L., Heitz, A., and Jouin, P., "Solid Phase Synthesis of Phosphonic Peptides", Tetrahedron Letters, 34(26): 4181–4184 (1993).

Grams, F., Dive, V., Yiotakis, A., Yiallouros, I., Vassiliou, S., Zwilling, R., Bode, W., Stocker, W., "Structure of astacin with a transition–state analogue inhibitor", Nature Structural Biology, 3(8): 671–675 (Aug. 1996).

Stocker, W., Grams, F., Baumann, U., Reinemer, P., Gomis- -Ruth, F.–X., McKay, D. B., Bode, W., "The metzincins– Topological and sequential relations between the astacins, adamalysins, serralysins, and matrixins (collagenase) define a superfamily of zinc–peptidases", Protein Science, 4: 823–840 (1995).

Stocker, W., Gomis–Ruth, F.–X., Bode, W., Zwilling, R., "Implications of the three–dimensional structure of astacin for the structure and function of the astacin family of zinc–endopeptidases", Eur. J. Biochem., 214: 215–231 (1993).

Janitz, M., Heiser, V., Bottcher, U., Landt, O., Lauster, R., "Three alternatively spliced variants of the gene coding for the human bone morphogenetic protein–1", J. Mol. Med., 76: 141–146 (1998).

Li, S.–W., Sieron, A. I., Fertala, A., Hojima, Y., Arnold, W. V., Prockop, D. J., "The C–proteinase the processes procollagens to fibrillar collagens is identical to the protein previously identified as bone morphogenic protein–1", Proc. Natl. Acad. Sci. USA, 93: 5127–5130 (1996).

Burchardt, E. R., Schroder, W., Heke, M., Kohlmeyer, J., Neumann, R., Kroll, W., "Expression Cloning of C–Terminal Procollagen (III) Propeptide and its use in a Novel Serum Assay to Monitor Liver Fibrosis", Hepatology, 26(4): 487A (1997). Abstract # 1435.

Kauschke, S. G., Knorr, A., Olzen, M., Burchardt, E. R., "Expression of Collagne (III) as Determined by Quantitative PCR and its Correlation with Extracellular Collagen Deposition in the Rat CCL Model of Liver Fibrosis", Hepatology, 538(A) (Oct. 1997) Abstract 1638.

Amano, S., Takahara, K., Gerecke, D., Nishiyama, T., Lee, S., Greenspan, D. S., Burgeson, R. E., "Bone Morphogenetic Protein–1 is the Processing Enzyme for Laminin 5 in Human Keratinocytes", Mol. Biol. Cell, 58A (1996) Abstract 338.

Senoo, H., Wake, K., "Suppression of Experimental Hepatic Fibrosis by Administration of Vitamin A", Lab. Invest., 52(2): 182–194 (1985).

PHOSPHINATE PEPTIDE ANALOGS FOR THE TREATMENT OF FIBROTIC DISORDERS

The invention relates to the use of phosphinate-peptide analogs, as inhibitors of procollagen C-proteinase (PCP), for treating fibrotic diseases.

It is known that procollagen C-proteinase (PCP) is a key enzyme in fibrogenesis. It catalyzes the hydrolytic elimination of the procollagen propeptides from procollagens I, II, III and IV and also laminin V [cf. Amano S, Takahara K; Gerecke D, Nishiyama T, Lee S, Greenspan D S, Burgeson R E: Bone morphogenetic protein-1 is the processing enzyme for laminin 5 in human keratinocytes, Mol. Biol. Cell 7 (suppl.) 58A (1996)]. Consequently, PCP is a key enzyme in collagen processing [cf. Olsen B J: Morphogenesis: collagen it takes and bone it makes, Curr. Biol. 6: 645–647 (1996)]. It was demonstrated in BMP-I knock-out mice that complete absence of PCP leads to incomplete collagen processing with the deposition of atypical, loose collagen fibrils [cf. Suzuki N, Labosky P A, Furata Y, Hargett I, Dunn R, Fogo A B, Takahara K, Peters D M, Greenspan D S, Hogan B L: Failure of ventral body wall closure in mouse embryos lacking a procollagen C-proteinase encoded by BMP-1, a mammalian gene related to Drosophila tolloid, Development 122: 3587–3595 (1996)].

PCP is probably also responsible for the hydrolytic elimination of the propeptide sequence of lysyl oxidase. The elimination of the prosequence probably leads to the activation of the catalytic lysyl oxidase activity of the mature form [cf. Pachenko M V, Stetler-Stevenson W G, Trubetskoy O V, Gacheru S N, Kagan H M: Metalloproteinase activity secreted by fibrogenic cells in the processing of prolysyl oxidase. Potential role of procollagen C-proteinase, J. Biol. Chem. 271: 7113–7119 (1996)]. Active lysyl oxidase covalently links opposing collagen fibrils to each other. In this way, PCP also indirectly increases the biological stability of the collagen towards degradation by collagenases.

PCP, or closely related proteins, appear also to play a role in the release of TGFβ-type growth factors. Recent studies have shown that PCP-like proteases are able to liberate TGFβ-type growth factors from an inactive complex with TGFβ-binding proteins [cf. Marques G, Musacchio M, Shimell M J, Wümenberg-Stapleton K, Cho K W Y, O'Connor M B: Production of a DPP activity gradient in the early drosophila embryo through the opposing actions of the SOG and TLD proteins, Cell 91: 417–426 (1997); Blader P, Rastegar S, Fischer N, Strähle U: Cleavage of the BMP antagonist chordin by zebrafish tolloid, Science 278: 1937–1949 (1997)]. In this case, the binding partner for the TGFβ-type growth factors is decomposed by means of specific proteolysis. Consequently, PCP may possibly also indirectly possess a TGFβ-type agonistic activity. PCP can therefore be ascribed a crucial role in fibrogenesis.

PCP activity has its origin in splicing variants of the BMP-I gene [cf. Kessler E, Takahara K, Biniaminow L, Brusel M, Greenspan D S: Bone morphogenetic protein-1: The type I procollagen C-proteinase, Science 271: 360–362 (1996)); Reddi A H: BMP-1: Resurrection as procollagen C-proteinase, Science 217: 463 (1996); Li S W, Sieron A L, Fertala A, Hojima Y, Arnold W V, Prockop D J: The C-proteinase that processes procollagens to fibrillar collagens is identical to the protein previously identified as bone-morphogenetic protein-1. Proc. Natl. Acad. Sci. USA 93: 5127–5130 (1996)]. It is so far definitely known that splicing variants BMP-I-I and BMP-I-III (tld variant) are able to cut procollagen and pro-lysyl oxidase specifically. While relatively recent studies have identified further BMP-1 splicing variants, the biological function and substrate specificity of the latter have not yet been fully elucidated [cf. Janitz M, Heiser V, Böttcher U, Landt O, Lauster R: Three alternatively spliced variants of the gene coding for the human bone morphogenetic protein-1. J. Mol. Med. 76: 141–146 (1998)].

Although success has so far only been achieved in expression-cloning and purifying PCP in small yields, a large number of structural details of the enzyme are known. Thus, PCP belongs to the family of astacin proteases. The crystal structure of astacin is known in detail. There is a very high degree of structural homology between the catalytic domain of BMP-I and astacin such that it has been possible, on the basis of this homology, to assign to many amino acids in the PCP protease domain their probable structural and biochemical function [cf. Stöcker W, Gomis-Rüth F X, Bode W, Zwilling R: Implications of the three-dimensional structure of astacin for the structure and function of the astacin family of zinc-endopeptidases, Eur. J. Biochem. 214: 215–231 (1993)].

In the past, it has been possible, by means of computer-guided molecular modeling, to infer the binding of substate to the active center of the astacings in molecular detail [cf. Stöcker W, Grams F, Baumann U, Reinemer P, Gomis-Rüth FX, McKay DB, Bode W: The metzincin—Topological and sequential relations between the astacins, adamalysins, serralysins, and matrixins (collagenases) define a superfamily of zinc-edopeptidases, Prot Sci.: 823–840 (1995)]. These studies led to the rational design of phosphinate-peptide analogs which inhibit astacin with a high degree of potency. The complex between a phosphinate inhibitor and astacin has been strutually elucidated ([cf. Grams F, Dive V, Yiotakis A, Yiallouros I, Vassilou S, Zwilling R, Bode W, St öcker W: Structure of astacin with transition-state analogue inhibitor, Nature Struct. Biol. 3: 671–675 (1996)].

Despite the high degree of structral homology between astacin and the catalytic domain of BMP-1, it has so far been assumed that, because of biochemical differences with regard to their reaction behavior and also in their ability to be inhibited by protease inhibitors, the two proteases are in fact markedly different. For example, there are biochemical differences between astacin and BMP-I with regard to their substrate specificity (as a crayfish digestive enzyme, astacin hydrolyzes collagen-like proteins relatively nonspecifically whereas PCP cuts highly specifically at only one site in the procollagen molecule and in pro-lysyl oxidase).

To date, only low-potency inhibitors of PCP, to which an antifibrotic effect is attributed, have been described in the literature [cf. Brenner M, Ho W B: C-proteinase inhibitors for the treatment of disorders related to the overproduction of collagen. WO 97/05865].

It has now been found, surprisingly, that phosphinate-peptide analogs of the general formula (I), in which
R[1] represents hydrogen or methyl,
and their salts and isomers inhibit PCP with a very high degree of potency and can therefore be used for the treatment and prophylaxis of fibrotic diseases.

Within the context of the invention, preference is given to physiologically harmless salts. In general, physiologically harmless salts are salts of the compounds according to the invention with inorganic or organic acids. Preference is given to salts with inorganic acids, such as hydrochloric acid, hydrobromic acid, phosphoric acid or sulfuric acid, or salts with organic carboxylic or sulfonic acids, such as acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid.

The compounds according to the invention can exist in stereoisomeric forms which either relate to each other as image and mirror image (enantiomers) or which do not relate to each other as image and mirror image (diastereomers). The invention also relates to the antipodes and to the racemic forms as well as to the diastereomeric mixtures.

The compounds of the general formula (I) can be present in all the enantiomeric and diastereomeric forms. Preference is given to those isomers in which the parts of the molecule formed from proline, lysine and leucine possess the L configuration, as well as to their salts and prodrugs.

Particular preference is given to using phosphinate-peptide analogs of the general formula (I), which have the configuration as shown, in which
R[1] represents hydrogen or methyl,
and their salts and isomers for the treatment and prophylaxis of fibrotic diseases.

Very particular preference is given to using the compound of the general formula (Ib)

designated Z-PKF(PC)APL-O-Me in that which follows, and its enantiomers and its salts for the treatment and prophylaxis of fibrotic diseases.

The compounds of the general formula (I) are known and can in principle be prepared from corresponding phosphinate compounds using customary methods of peptide synthesis [cf., in this regard, Yiotakis A, Vassilio S, Jiracek J, Dive V: Protection of the Hydroxyphosphinyl Function of Phosphinic Dipeptides by Adamantyl. Application to the Solid-Phase Synthesis of Phosphinic Peptides, J. Org. Chem. 61: 6601–6605 (1996); Campagne J M, Coste J, Guillou L, Heitz A, Jouin P: Solid phase synthesis of phosphinic peptides, Tetrahedron Lett. 34: 4181–4184 (1993)].

The results were unexpected because BMP-I, meprin and astacin differ from each other, in particular, in the so-called S1' loop. A sector from this loop is depicted here:

astacin: T-DPYD
BMP-I: KPPIG-Q
meprin: I-IG-Q

This loop forms the essential part of the S1' binding pocket of the astacin-like proteases. It is here, as has been shown using the example of astacin and meprin, that the key to the differing substrate and inhibitor specificities of the two enzymes lies. Meprin and astacin differ very markedly from each other in the S1' pocket. PCP additionally has two proline residues and one lysine residue in this region. As has been shown by computer modeling the protease domain of PCP, the lysine residue is very probably involved in binding the carboxyl group in the side chain of the aspartate in P1' next to the cleavage site in the procollagen. According to the model, the proline residues are in the cis configuration and represent a peculiarity of the BMP-I subfamily among the astacins. By contrast, astacin does not cleave next to acidic residues. For these reasons, it was completely unexpected that a phosphinate which was designed for inhibiting astacin [cf Yiallouros I, Vassiliou S, Yiotakis A, Zwilling R, Stöcker W, Dive V: Phosphinic peptides, the first potent inhibitors of astacin, behave as extremely slow-binding inhibitors, Biochem. J. 331: 375–379 (1998)] would prove to be an effective PCP inhibitor.

The compounds of the general formula (I) according to the invention exhibit a valuable pharmacological activity spectrum which it was not possible to foresee.

Surprisingly, the compounds according to the invention are notable for having a very high potency when inhibiting PCP.

The compounds according to the invention are therefore suitable for treating liver fibroses of any genesis and fibroses which are manifested in other organs.

These fibroses include various groups of diseases which are accompanied by a qualitative change in collagen production or by an increased deposition of collagen in the extracellular space, such as liver fibroses of differing origin, such as alcoholic liver cirrhosis, biliary cirrhosis, hepatitis of viral or other genesis, idiopathic interstitial fibroses, idiopathic lung fibroses, acute pulmonary fibroses, acute respiratory distress syndrome (ARDS), perimuscular fibroses, pericentral fibroses, dermatofibromas, kidney fibroses, diabetic nephropathy, glomerulonephrites, systemic or local scleroderma, keloids, hypertrophic scar formation, joint adhesions, arthroses, myelofibroses, cicatrization of the cornea, cystic fibrosis, muscular fibroses, Duchenne's muscular dystrophy, strictures of the esophagus, Omond's disease, Crohn's disease, ulcerative colitis and aneurysms of the large vessels.

In addition, the invention encompasses fibrotic diseases which are initiated or provoked by surgical scar revisions, plastic surgery, glaucoma, cataract fibroses, cicatrizations of the cornea, graft-versus-host disease, surgical interventions performed on tendons, nerve trapping syndromes, Dupuytren's contracture, adhesions resulting from gynecological interventions, pelvic adhesions, epidural fibroses, and diseases of the thyroid gland or the parathyroid glands, and also by metastatic bone invasion, by multiple myeloma or by restenoses.

Detecting PCP Activity in a Fluorescence Sequencing Test

For the purpose of detecting PCP activity, a synthetic decapeptide substrate having the sequence

DABCYL-Asp-Phe-Tyr-Arg-Ala-Asp-Glen-Pro-Arg-Asp (EDANS)-NH$_2$ was cleaved by adding PCP. This peptide frequency corresponds to the region in procollagen $\alpha_2$(I) which is cleaved by PCP. The cleavage sequence is known to biochemical experts [cf. Lee S T, Kessler E, Greenspan D S: Analysis of site-directed mutations in human pro-$\alpha_2$(I) collagen which block cleavage by the C-proteinase, J. Biol. Chem. 265: 21992–21996 (1990)], as is the dequenching test method [cf. Matayoshi E D, Wang G T, Krafft G A, Erickson J: Novel fluorogenic substrates for assaying retroviral proteases by resonance energy transfer, Science 247: 954–958 (1989)].

The concentration of the synthetic peptide was 5.6 µM, while the final buffer conditions were: 50 mM tris, pH 7.5, 150 mM NaCl and 0.005% Brij35.

The kinetic test was carried out in the following manner: the fluorescence substrate was dissolved in 90 µl of reaction buffer. The kinetics of the conversion of the substrate by PCP were detected, in duplicate determinations, by measuring the fluorescence (ex. 355 nm/em. 538 nm) at from 0 to 120 min. The reaction was started by adding a suitable activity of PCP dissolved in 10 µl of reaction buffer. The emission, as a measure of the proteolytic activity, was measured at time intervals of initially 5 min and then subsequently at longer time intervals. The spontaneous decomposition of the fluorescence substrate in the added presence of reaction buffer lacking PCP activity was measured as the negative control. The fluorescence measurements took place at 37° C. over a period of approx. 4 h. After the reaction had come to an end, the substrate was completely decomposed by adding proteinase K (Boehringer Mannheim, 1.44 µg per reaction mixture, dissolved in 10 µl of PBS) and incubating at 37° C. for 20 min. The fact that the hydrolysis was complete was shown by there being no further increase in the fluorescence with time.

The relative conversion of substrate in % of the total quantity was calculated from:

% conversion=$(F_t-F_{-t}) \div (F_{total}-F_{in1}) \times 100\%$ where $F_t$ is the relative fluorescence after a time interval t while incubating with PCP. $F_{-t}$ is the corresponding relative fluorescence after the time interval t without PCP being added, $F_{total}$ is the fluorescence following total hydrolysis produced by adding proteinase K, and $F_{in1}$ is the initial relative fluorecence before starting the reaction by adding proteinase K.

In the test, the PCP activity used was typically adjusted such that approx. 20% of the substrate was converted by inhibited enzyme within the measurement period.

Figure 1:
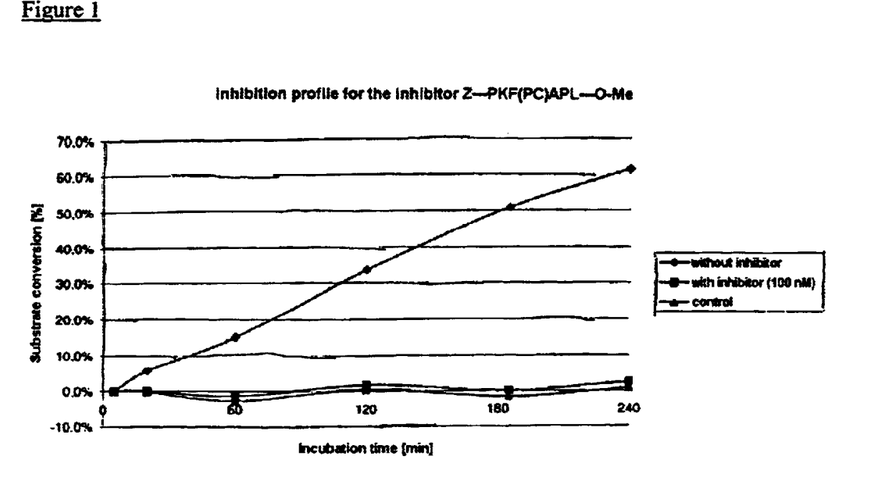
FIG. 1 shows the transformation of the DABCYL-EDANS-decapeptide substrate by recombinant PCP as a function of time. The enzyme activity is almost completely inhibited in the presence of 100 nM inhibitor.

FIG. 1 shows typical reaction kinetics (% conversion) which were obtained when adding the phosphinate inhibitor Z-PKF(PC)APL-O-Me.

The percentage inhibition obtained in the added presence of the inhibitors was calculated as follows:

% inhibition=100%×% conversion (with inhibitor)÷% conversion (without inhibitor)

Figure 2:
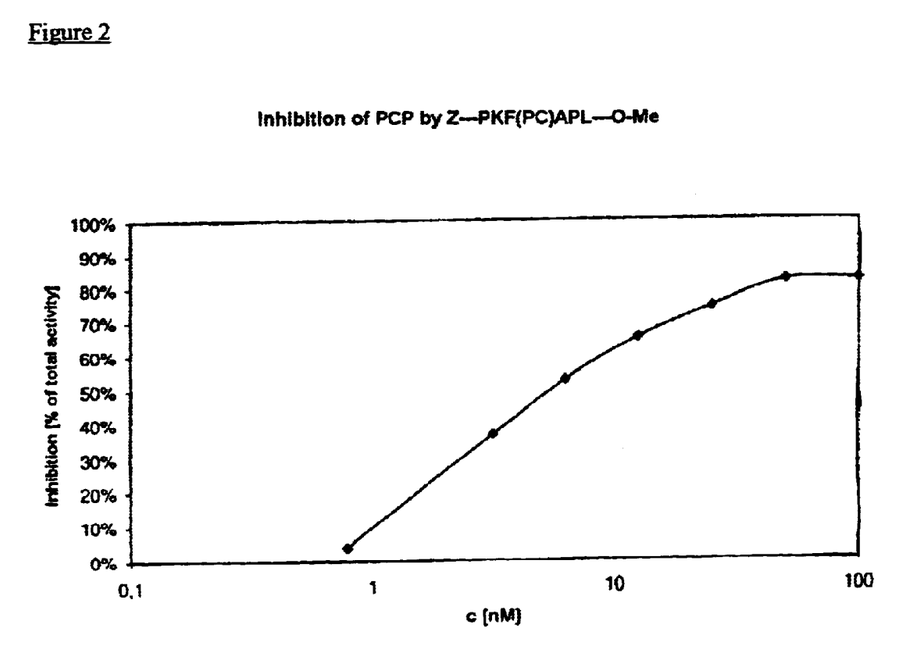
FIG. 2 shows the concentration-effect relationship of the phosphinate inhibitor Z-PKF(PC)APL-O-Me.

FIG. 2 depicts the concentration-effect relationship of a phosphinate inhibitor.

Determining the Specificity of PCP Inhibitors by Carrying Out in-vitro Investigations Using the Astacin-like Protease Meprin Meprin is an enzyme which belongs to the astacin protease family and which is found in humans (Stöcker W, Gomis-Rüth F X, Bode W, Zwilling R: Implications of the three-dimensional structure of astacin for the structure and function of the astacin family of zinc-endopeptidases, Eur. J. Biochem. 214: 215–231 (1993)). The meprin activity test was carried out in a completely analogous manner to the in-vitro assay for measuring PCP activity. Instead of the recombinant PCP, use was made of human meprin, which also transforms the fluorescence-labeled decapeptide.

Figure 3:
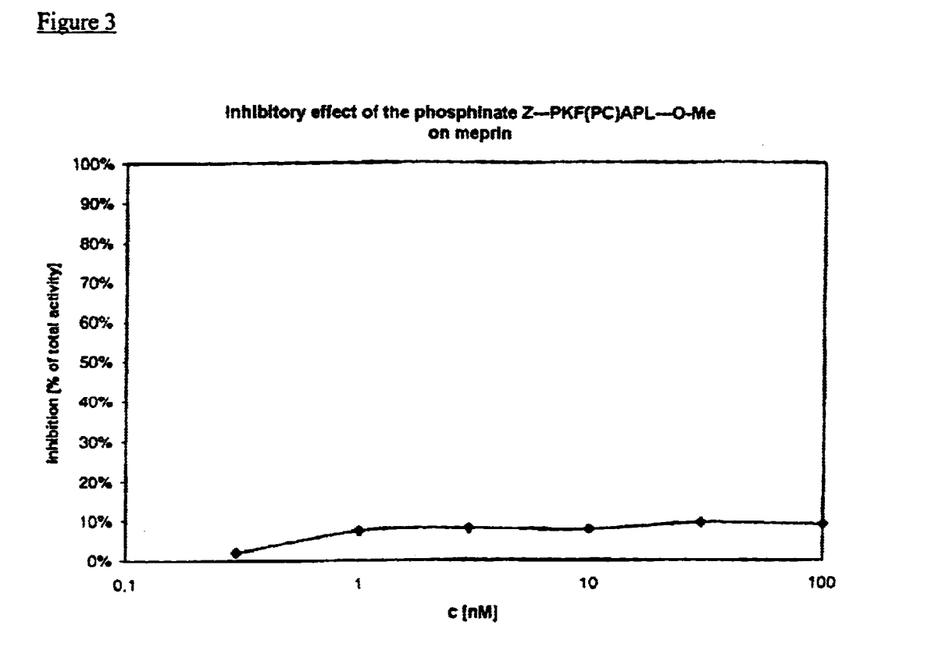
FIG. 3 shows the specificity of the highly active phosphinate-peptide analog Z-PKF(PC)APL-O-Me for PCP. Even at concentrations of up to 100 nM, meprin is only slightly inhibited, in a dose-dependent manner, in its transformation of the fluorescence-labeled peptide.

FIG. 3 shows the specificity of the highly active phosphinate-peptide analog Z-PKF(PC)APL-O-Me for PCP. Even at concentrations of up to 100 nM, meprin is only slightly inhibited (in a dose-dependent manner) in its transformation of the fluorescence-labeled peptide.

Demonstration of Biological Activity

The biological activity of the substances can be demonstrated in cell culture assays and in vivo. For example, after administering the inhibitors, it is possible, in human cell lines, to measure the decline in the concentration of free procollagen $\alpha_1$(III) propeptide in the supernatants, because this peptide is released by PCP activity. The PIIICP concentrations in the supernatant can be measured using a recently established assay [cf. Burchardt E R, Schröder W, Heke M, Kohlmeyer J, Neumann R, Kroll W: Expression cloning of C-terminal procollagen (III) propeptide and its use in a novel serum assay to monitor liver fibrogenesis, Hepatology 26: 487A (1997)].

In order to demonstrate the antifibrotic effect of the substances in the liver, it is possible, for example, to use the animal model of acute [cf. Johnson S J, Hines J E, Burt A D: Phenotypic modulation of perisinusoidal cells following acute liver injury: a quantitative analysis. Int. J. Exp. Path 1992; 73: 765–772 (1992)] or chronic [cf. McLean E, McLean A, Sutton P: Instant Cirrhosis. An improved method for producing cirrhosis of the liver in rats by simultaneous administration of carbon tetrachloride and phenobarbitone, Br. J. Exp. Pathol. 1969; 50: 502–506 (1969)] carbon tetrachloride-induced liver damage, the model of liver fibrosis due to bile duct ligature [cf. Kountouras J, Billing B, Scheuer P: Prolonged bile obstruction: a new experimental model for cirrhosis in the rat, Br. J. Exp. Pathol. 1984; 65: 305–311 (1984)] or the liver fibrosis which is induced by hetemlogous serum [cf. Bhunchet E, Wake K.: Suppression of experimental hepatic fibrosis by administration of vitamin A, Lab. Invest 1985; 52: 182–194 (1984)]. It is also possible to use other animal models in which liver fibrosis occurs for demonstrating the antifibrotic effect.

Depending on the organ in which the fibrosis is manifested, or on the nature of the fibrotic damage, it is also possible to use animal models for other manifestations of fibrosis, for example in the heart, in the kidneys, in the lungs, in the skin or in other organs.

The reduction in collagen deposition can be demonstrated, for example, by determining the content of hydroxyproline [cf. Gerling B, Becker M, Waldschmidt J, Rehmann M, Schuppan D.: Elevated serum aminoterminal procollagen type-III-peptide parallels collagen accumulation in rats with secondary biliary fibrosis, Hepatology 1996; 25: 79–84 (1996)] in the fibrotic organs or by means of quantitative morphometry [cf. Kauschke S G, Knorr A, Olzen M, Burchardt E R: Expression of collagen (III) as determined by quantitative PCR and its correlation with extracellular collagen deposition in the rat $CCl_4$ model of liver fibrosis. Hepatology 26: 538A (1997)].

The present invention also includes pharmaceutical preparations which, in addition to inert, nontoxic, pharmaceutically suitable adjuvants and excipients, also comprise one or more compounds of the general formula (I), or which consist of one or more active compounds of the formulae (I), and also processes for producing these preparations.

In these preparations, the active compounds of the formulae (I) should be present at a concentration of from 0.1 to 99.5% by weight, preferably of from 0.5 to 95% by weight, of the total mixture.

In addition to the active compounds of the formulae (I), the pharmaceutical preparations can also comprise other pharmaceutical active compounds.

The abovementioned pharmaceutical preparations can be produced in a customary manner using known methods, for example using the adjuvant(s) or excipient(s).

In general, it has proved to be advantageous, in order to achieve the desired result, to administer the active compound(s) of the formulae (I) in total quantities of from about 0.01 to about 100 mg/kg, preferably in total quantities of from about 1 mg/kg to 50 mg/kg of body weight per 24 hours, where appropriate in the form of several individual doses.

However, it can, where appropriate, be advantageous to deviate from the said quantities, depending on the nature and body weight of the individual being treated, on the individual response to the drug, on the nature and severity of the disease, on the nature of the preparation and its administration, and on the time or time interval at which the administration is effected.

The preparation of the compounds of the formula (I) according to the invention is demonstrated below with the aid, by way of example, of an exemplary synthesis of the compound of the formula (I, R=methyl), to which the present invention is not, however, limited. Unless otherwise stated, all the quantity data given below refer to percentages by weight.

Ex. 1a (1R)-1{[(Benzyloxy)carbonyl]amino}2-phenylethyl{3[(2S)-2-({[(1S)-1-(methoxycarbonyl)-3-methylbutyl]amino}carbonyl)tetrahydro-1H-pyrrol-1-yl]-2-methyl-3-oxopropyl}phosphinic acid 4.0 eq. of ethyldiisopropylamine, 1.50 eq. of benzotriazol-1-yl-oxy-tris-pyrrolidino-phosphonium hexafluorophosphate (PyBop) (J. Martinez et al., J. Med. Chem. 1988, 28, 1874; J. Costre, D. Le-Nguyen, B. Castro, Tetrahedron Lett., 1990, 31, 2055) and, after from 2 to 5 min. 1.0 eq. of Pro-Leu-OMe-trifluoroacetic acid salt (prepared using standard methods of peptide chemistry, cf., e.g., Houben-Weyl, 4th edtn: Methoden der Organlschen Chemie (Methods in organic chemistry), Volume XVt-/-2, Synthese von Peptiden Teil 1 und Teil 2 (Synthesis of peptides, Part 1 and Part 2), Georg Thiems Verlag, Stuttgart 1974) are added, one after the other, at 0° C. and under argon, to a solution of from 1.4 to 1.5 eq. of [(1-benzyloxcarbonyl)amino]2-phenylethyl)-2-carboxy- 1-propyl)hydroxyphosphonic acid (prepared in analogy with WO 89/10961, p. 72, Ex. [14]) in absolute dichloromethane (from approx. 0.1 to 0.15 mol/l). After 15–30 min, the ice cooling is removed and the mixture is stirred overnight at room temperature. It is then diluted with dichloromethane and washed consecutively with saturated sodium hydrogen carbonate solution, 1N hydrochloric acid solution and saturated sodium chloride solution, dried over magnesium sulfate and concentrated in vacuo.

Yield: 133.7 mg of a yellowish oil as the crude product (no yield given since the product contains solvent residues) LC-MS: rt (%), m/z (%)=4.066 (34.6%), 630 (100, M+H); 4.197 (52.7), 630 (100, M+H).

Ex. 1b (1R)-1-Amino-2-phenylethyl{3-[(2S)-2-({[(1S)-1-(methoxycarbonyl)-3-methylbutyl]amino}carbonyl)tetrahydro-1H-pyrrol-1-yl]-2-methyl-3-oxopropyl}phosphinic acid The protected amine derivative from Ex. 1a is dissolved in ethanol (approx. 0.05 mol/l), after which a catalyst (10% palladium on charcoal) is added to the solution under argon. The suspension is stirred vigorously at room temperature and under an $H_2$ atmosphere (normal pressure) for approx. 2 hours before being filtered through celite (subsequently washed thoroughly with ethanol). The filtrate is concentrated in vacuo and dried under high vacuum.

Yield: 80.4 mg (97.3% of theory) LC-MS: rt, m/z (%)= 2.706,496 (100, M+H) HPLC: rt (%)=5.80 (32.5), 5.91 (51.5).

Ex. 1c (1R)-1-({(2S)-2-{[(Benzyloxy)carbonyl]amino}-6-[(tert-butoxy-carbonyl)amino]hexanoyl}amino)-2-phenylethyl{3-[(2S)-2-({[(1S)-1-(methoxycarbonyl)-3-methylbutyl]amino}carbonyl)tetrahydro-1H-pyrrol-1-yl]-2-methyl-3-oxopropyl}phosphinic acid 4.0 eq. of ethyldiisopropylamine, 1.50 eq. of PyBop and, after from 2 to 5 min, 1.45 eq. of Z-(NHBoc)-Lys-OH are added, one after the other, at 0° C. and under argon, to a solution of 1.0 eq. of the compound from Ex. 1b. After 15–30 min, the ice cooling is removed and the mixture is stirred overnight at room temperature. It is diluted with dichloromethane and consecutively washed with saturated sodium hydrocarbonate solution, 1N hydrochloric acid solution and saturated sodium chloride solution, dried over magnesium sulfate and concentrated in vacuo. Crude yield: 207 mg of a viscous oil, LC-MS: rt (%), m/z (%)=4.456 (11.2%), 858 (100, M+H); 4.549 (32.7), 858 (100, M+H). The crude product is purified by means of preparative RP-HPLC.

Yield: 40 mg (32.8% of theory).

Ex. 1d (1R)-1-({(2)-2-Amino-6[tert-butoxycarbonyl)amino]hexanoyl}-amino)-2-phenylethyl{3-[(2S)-2-({[(1S)-1-(methoxycarbonyl)-3-methylbutyl]amino}carbonyl)tetrahydro-1H-pyrrol-1-yl]-2-methyl-3-oxopropyl}phosphinic acid The protected amine derivative from Ex. 1c is dissolved in ethanol (approx. 0.05 mol/l), after which a catalyst (10% palladium on charcoal) is added to the solution under argon. The suspension is stirred vigorously at room temperature and under an $H_2$ atmosphere (normal pressure) for approx. 2 hours before being filtered through celite (subsequently washed thoroughly with ethanol). The filtrate is concentrated in vacuo and dried under high vacuum.

Yield: 31 mg (85.4% of theory) LC-MS: rt (%), m/z (%)=2.97 (85.8%), 724 (100, M+H).

Ex. 1e

(1R)-1-({(2)-2-Amino-6[tert-butoxycarbonyl)amino]hexanoyl}-amino)-2-phenylethyl{3-[(2S)-2-({[(1S)-1-(methoxycarbonyl)-3-methylbutyl]amino}carbonyl)tetrahydro-1H-pyrrol-1-yl]-2-methyl-3-oxopropyl}phosphinic acid

4.0 eq. of ethyldiisopropylamine, 1.50 eq. of PyBop and, after from 2 to 5 min, 1.45 eq. of Z-Pro-OH are added, one after the other, at 0° C. and under argon, to a solution of 1.0 eq. of the compound from Ex. 1d. After 15–30 min, the ice cooling is removed and the mixture is stirred overnight at room temperature. It is diluted with dichloromethane and washed consecutively with saturated sodium hydrocarbonate solution, 1N hydrochloric acid solution and saturated sodium chloride solution, dried over magnesium sulfate and concentrated in vacuo. 50 mg of crude product are obtained. LC-MS: rt (%), m/z (%)=4.394 (25.9%), 955 (100, M+H); 4.509 (44.6), 955 (100, M+H). The crude product is purified by means of preparative RP-HPLC.

Yield: 24.5 mg (59.9% of theory).

Ex. 1f: Preparation of the Compound of the Formula (I). R=methyl (1R)-1-({(2S)-6-amino-2-[({(2S)-1-[(benzyloxy)carbonyl]tetrahydro-1H-pyrrol-2-yl}carbonyl)amino]hexanoyl}amino)-2-phenylethyl{3-[(2S)-2-({[(1S)-1-(methoxy-carbonyl)3-methylbutyl]amino}carbonyl)tetrahydro-1H-pyrrol-1-yl]-2-methyl-3-oxopropyl}phosphinic acid 0.3 ml of trifluoroacetic acid is added dropwise to 24.50 mg (0.03 mmol) of the compound from Ex. 1e in an ice-cooled mixture consisting of 0.3 ml of methylene chloride and 0.03 ml of water. The cooling is removed and the mixture is stirred at room temperature for two hours before being concentrated in vacuo and the residue being thoroughly dried under high vacuum.

Yield: 21.0 mg of a colorless solid (95.8% of theory) LC-MS: rt, m/z (%)=3.057 (both stereoisomers), 855 (100, M+H) RP-HPLC rt (%)=2.18 (48.7), 2.42 (46.0).

---

---

What is claimed is:

1. A method of treating a fibrotic disease, comprising administering to a mammal an effective amount of a phosphinate-peptide analog of the general formula (I)

(I),

-continued in which $R^1$ represents hydrogen or methyl, and/or their stereoisomers and salts.

2. A method of treating a fibrotic disease, comprising administering to a mammal an effective amount of a phosphinate-peptide analog of the general formula (I) having the configuration shown in formula (Ia)

(Ia), in which
R[1] represents hydrogen or methyl, and/or their salts are used.

3. The method according to claim 1, comprising administering a compound of the formula (Ib)

(Ib)

and/or its salts.

4. The method according to claim 1, wherein said fibrotic disease is liver fibrosis.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Asp Phe Tyr Arg Ala Asp Gln Pro Arg Asp
1               5                   10